(12) United States Patent
Chervenak et al.

(10) Patent No.: US 8,912,494 B2
(45) Date of Patent: Dec. 16, 2014

(54) APPARATUS FOR ULTRASENSITIVE LONG-WAVE IMAGING CAMERAS

(75) Inventors: James A. Chervenak, Silver Spring, MD (US); Ari D. Brown, Baltimore, MD (US); Edward J. Wollack, Clarksville, MD (US); Dominic J. Benford, Potomac, MD (US)

(73) Assignee: The United States of America as represented by the Administrator of the National Aeronautics Space Administration, Washington, DC (US)

( * ) Notice: Subject to any disclaimer, the term of this patent is extended or adjusted under 35 U.S.C. 154(b) by 661 days.

(21) Appl. No.: 13/211,413

(22) Filed: Aug. 17, 2011

(65) Prior Publication Data

US 2013/0043394 A1    Feb. 21, 2013

(51) Int. Cl.
*G01J 5/00*    (2006.01)
*G01J 3/02*    (2006.01)
*G01J 5/08*    (2006.01)
*G01J 3/42*    (2006.01)
*G01J 5/20*    (2006.01)
*G01N 21/35*   (2014.01)

(52) U.S. Cl.
CPC .............. *G01J 3/0227* (2013.01); *G01J 5/0828* (2013.01); *G01J 3/42* (2013.01); *G01J 5/0837* (2013.01); *G01J 5/20* (2013.01); *G01N 21/3581* (2013.01)
USPC ................. 250/336.1; 250/338.1; 250/339.01

(58) Field of Classification Search
CPC ...... G01J 3/0227; G01J 5/0828; G01J 5/0837; G01J 5/20; G01J 3/42; G01N 21/3581
USPC .......................................... 250/338.1, 336.1
See application file for complete search history.

(56) References Cited

U.S. PATENT DOCUMENTS 6,242,740 B1 *   6/2001   Luukanen et al. ............. 250/353
2003/0222217 A1 * 12/2003   Luukanen ................... 250/336.2
2010/0182210 A1 *  7/2010   Ryou et al. ..................... 343/722

OTHER PUBLICATIONS

M.S. Kowitt, D. J. Fixsen, A. Goldin, and S. S. Meyer, Frequency Selective Bolometers, Oct. 1, 1996, Applied Optics vol. 35, No. 28, http://www.opticsinfobase.org/ao/abstract.cfm?uri=ao-35/28/5630, Retrieved Mar. 23, 2014.*
A. A. Eldek, A. Z. Elsherbeni, and C. E. Smith, Dual-Wideband Square Slot Antenna With a U-Shaped Printed Tuning Stub for Personal Wireless Communication Systems, 2005, Progress in Electromagnetics Research, vol. 53, http://www.jpier.org/pier/pierphp?paper=0410301, Retreived Apr. 1, 2014.*

* cited by examiner

*Primary Examiner* — David Porta
*Assistant Examiner* — Gisselle Gutierrez

(57) ABSTRACT

An apparatus for ultrasensitive long-wave imaging cameras is provided. In one embodiment, the apparatus includes a filter configured to allow high frequencies of interest to pass through the filter. The apparatus also includes an antenna that is configured to receive the high frequencies of interest. The apparatus further includes a plurality of bolometers that are configured to measure data regarding the high frequencies of interest.

17 Claims, 7 Drawing Sheets

APPARATUS FOR ULTRASENSITIVE LONG-WAVE IMAGING CAMERAS

ORIGIN OF THE INVENTION

The invention described herein was made by an employee of the United States Government and may be manufactured and used by or for the Government for Government purposes without the payment of any royalties thereon or therefore.

FIELD

The present invention relates to multicolor detectors and, more particularly, to multicolor detectors for ultrasensitive long-wave imaging cameras.

BACKGROUND

Terahertz (THz) imaging is a compelling and competitive area of research for building next generation instruments. There are two methods researchers have developed for optical coupling to ultrasensitive devices at THz frequencies. The first method is absorber coupling to detectors, which can be realized for example with a thermometer that measures heat and temperature changes in an electromagnetic absorbing media in the signal band. However, it is difficult to find materials that absorb frequencies uniformly across the THz frequencies that are stable and absorb at high efficiency. The second method is to antenna couple to detectors. However, antenna coupling has inefficiencies similar to the first method (broadband bolometer) and in its simplest implementation can only detect a single color. However, it should be appreciated that at microwave and millimeter frequencies, a frequency diplexor can be used to detect multiple colors. But, at THz frequencies, the ohmic loss and required tolerances make direct implementation of this solution prohibitive from a practical perspective.

The high-resolution airborne wideband camera (HAWC) currently takes images in separate THz bands with a mechanical filter wheel, requiring temporal separation of the maps of different bands on a moving aircraft. For example, HAWC consists of a large format THz imager that selects one of its four frequency bands by rotating the filter wheel. The need to image each wavelength separately sets an upper limit to the mapping speed and spectral throughput of the instrument.

Furthermore, on a moving airplane, fast mapping speed is critical for obtaining good spectral data because of the Earth's changing atmospheric conditions during flight and the integration time available during the relatively short flight duration. The imager's large pixels do not allow, for example, Nyquist sampling of the sky with the stratospheric observatory for infrared astronomy (SOFIA) telescope, and the technology currently employed is unable to fill the entire SOFIA focal plane.

SUMMARY

Certain embodiments of the present invention may provide solutions to the problems and needs in the art that have not yet been fully identified, appreciated, or solved by current antennas. For instance, embodiments described herein pertain to a quasioptical (QO) filter arrangement that can transmit one or more THz bands to uniformly couple to them to antennas, and can transmit a THz antenna read out by one or more bolometers (or detectors). This configuration allows for simultaneous imaging to enhance HAWC's mapping speed by a factor of ten and simplify image calibration and fidelity.

In accordance with an embodiment of the present invention, an apparatus is provided. The apparatus includes a filter configured to allow high frequencies of interest to pass through the filter. The apparatus also includes an antenna that is configured to receive the high frequencies of interest. The apparatus further includes a plurality of bolometers that are configured to measure data regarding the high frequencies of interest.

In accordance with another embodiment of the present invention, an apparatus is provided. The apparatus includes a quasioptical filter and an antenna. The quasioptical filter is configured to prevent frequencies below a cut-off from passing through the filter. The antenna has a single slot, which is configured with a plurality of tap points to receive and measure high frequencies of interest ranging between 1 terahertz and 10 terahertz.

In accordance with yet another embodiment of the present invention, an apparatus is provided. The apparatus includes a quasioptical filter and an antenna. The quasioptical filter is configured to prevent frequencies below a cut-off from passing through the filter. The antenna can have a plurality of slots. Each slot is configured with a plurality of tap points to receive high frequencies in order to allow measurements of high frequencies of interest ranging between 1 terahertz and 10 terahertz.

BRIEF DESCRIPTION OF THE DRAWINGS

For a proper understanding of the invention, reference should be made to the accompanying figures. These figures depict only some embodiments of the invention and are not limiting of the scope of the invention. Regarding the figures.

DETAILED DESCRIPTION OF THE EMBODIMENTS

It will be readily understood that the components of the present invention, as generally described and illustrated in the figures herein, may be arranged and designed in a wide variety of different configurations. Thus, the following detailed description of the embodiments of an apparatus, a system, a method, and a computer readable medium, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with the embodiment may be included in at least one embodiment of the present invention. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more embodiments.

Embodiments of the present invention pertain to an apparatus with a quasioptical filter arrangement that enables compact multicolor spectrum at a focal plane and THz antenna readout by up to three bolometers. The apparatus facilitates high efficiency by reducing microstrip (e.g., dielectric and ohmic) losses that are a limiting challenge at THz frequencies, and also facilitates pixel compactness by eliminating the need for bulky filters in the focal plane.

Figure 1:
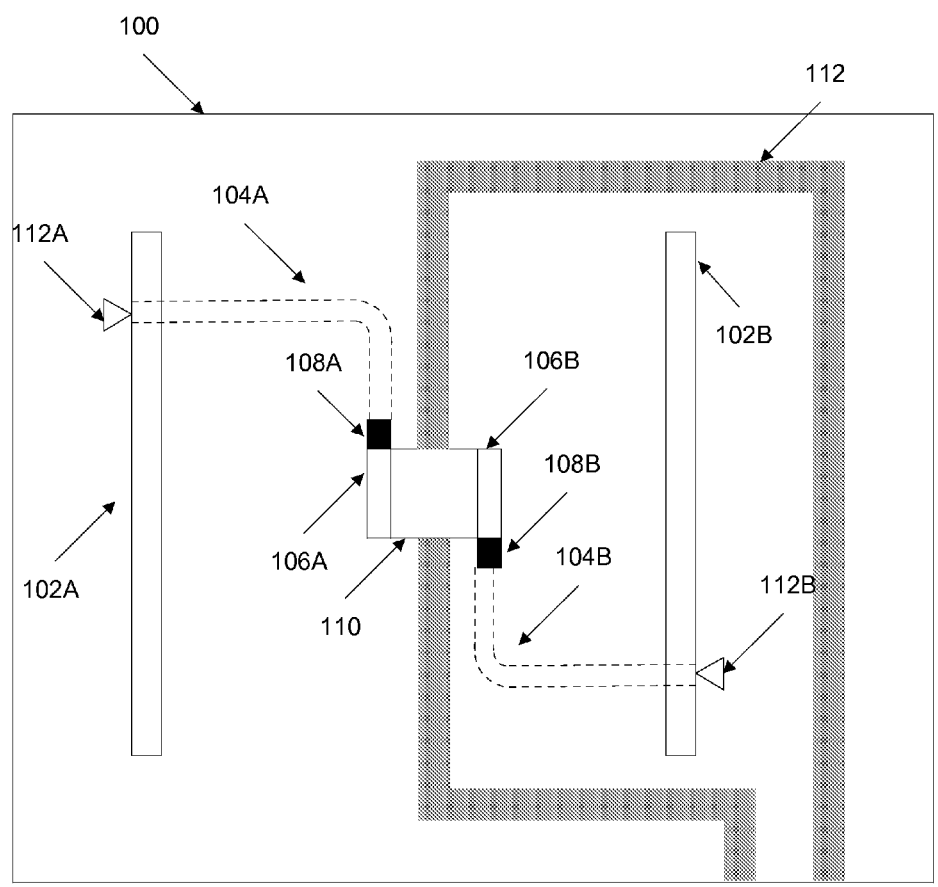
FIG. 1 illustrates a single color antenna with double slots, in accordance with an embodiment of the present invention.

FIG. 1 illustrates a single color antenna 100 with double slots, in accordance with an embodiment of the present invention. The configuration shown in FIG. 1 allows a single frequency to be read as there is a single detector placed on antenna 100. For example, this configuration allows measurements of THz radiation with the use of a small bolometer and two slots on the antenna.

Antenna 100 is comprised of a metal sheet and placed between a high resistivity silicon (Si) substrate, which is below the metal sheet, and a vacuum of space, or a dielectric antireflection (AR) coating, which is on top of the metal sheet. See FIG. 4 for more detail.

In this embodiment, the metal sheet has two antenna slots 102A and 102B. Slots 102A and 102B are separated by a distance $2(\lambda/n)$, where $\lambda$ represents the wavelength (i.e., the speed of light divided by frequency) and n represents an index over a fraction of the dielectric (e.g., a silicon dielectric) or the square root of the effective dielectric constant, $\in_{eff}^{1/2}$. A metal lead (or wiring) 104A, such as a gold (Au) metal lead, is placed across (or capacitively coupled to) slot 102A and another metal lead 104B is placed across slot 102B. However, it should be noted that both leads 104A and 104B can be capped by stubs 112A and 112B. Leads 104A and 104B are electrically connected to absorbers 106A and 106B, respectively. This configuration allows leads 104A and 104B to receive signals from slots 102A and 102B and to transmit the signals to absorbers 106A and 106B.

In this embodiment, with respect to the curves in leads 104A and 104B, the radius of curvature may be large compared to the width of the microstrip line. The layout and routing of the microstrip transmission lines strives to minimize the total microstrip line length in order to minimize ohmic and dielectric signal losses. The microstrip line length between the slot tap points and the power combiner (the microstrip "T" junction; see for example FIG. 2, 204C) before the bolometer may be of equal length (electrical delay) so the antenna is appropriately sampled. The orientation of the microstrip relative to the slot can produce the desire antenna response. It should be appreciated that the antenna shown in FIG. 1 can be viewed as an array with two halfwave slots that feed out of phase as a result of the microstrip tap points on the line.

In this embodiment, superconducting plugs 108A and 108B are situated between leads 104A and 104B and absorbers 106A and 106B, respectively, and are configured to prevent electrons from diffusing as the electrons are absorbed by absorbers 106A and 106B. However, it should be appreciated that depending on the configuration of antenna 100, superconducting plugs 108A and 108B may not be utilized in other embodiments.

FIG. 1 also shows that absorbers 106A and 106B are intimately electrically in contact with an electron-phonon decoupling (EPD) transition edge sensor (TES) (or zeptobolometer) 110. Because absorbers 106A and 106B are electronically coupled to bolometer 110, data from absorbers 106A and 106B can be read by bolometer 110. In other words, bolometer 110 is configured to read out a signal from the impedance matched resistor or absorber. Readout wiring 112 is connected to bolometer 110 and is configured to bias bolometer 110 such that if there is a small change in the current provided by the hot electrons, then an amplifier (not shown) can measure the change in the current.

For instance, as terahertz radiation illuminates antenna 100, slots 102A and 102B are configured to receive or absorb the light via absorbers 106A and 106B. As hot electrons are decoupled from the phonons, the hot electrons are conveyed to bolometer 110 via absorbers 106A and 106B. The heat from the hot electrons is read by bolometer 110 and transmitted to an amplifier (not shown) by readout wiring 112. As a result, the amplifier (not shown) is configured to measure the data read by bolometer 110.

Figure 2:
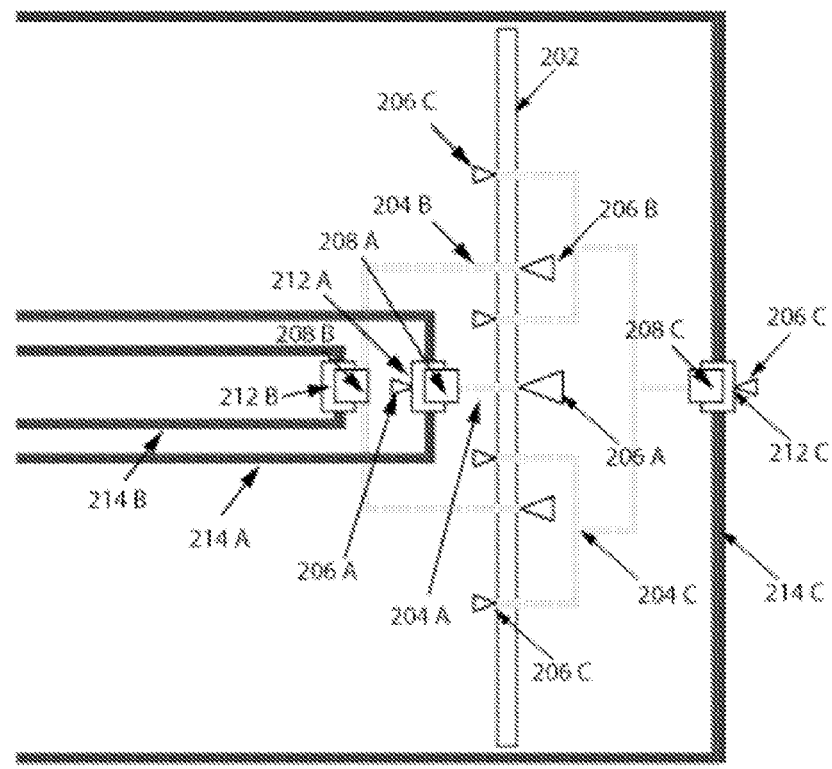
FIG. 2 illustrates a multicolor antenna with a single slot, in accordance with another embodiment of the present invention.

FIG. 2 illustrates a multicolor antenna 200 with a single slot, in accordance with another embodiment of the present invention. Antenna 200 is comprised of a slot 202 in a ground plane with a tap as an antenna feed point. It should be appreciated that if the antenna is detecting signals of less than the superconducting transition frequency, then a superconducting ground plane may be used (e.g., for niobium this occurs at ~700 GHz). However, for signals above the superconducting transition frequency, high quality thin metal films that are non-superconducting can be used as the ground plane.

In this embodiment, antenna 200 has a single slot 202 having a length of $\lambda_{max}/\in_{eff}^{1/2}$, where $\lambda_{max}$ represents the largest wavelength intended to detect more than one frequency and $\in_{eff}^{1/2}$ (or n) represents the square root of the effective dielectric constant. A plurality of leads 204A, 204B, and 204C are placed across slot 202 and are capped by stubs 206A, 206B, and 206C, respectively. Each stub (radial) acts as a tap point for the slot line antenna whose position is selected to ensure that each lead samples the desired frequency or mode. It may be appreciated that, in some embodiments, the orientation of the tap point with respect to the slot allows for appropriate sampling of the antenna's response given the symmetry of the mode. In other embodiments, it may be desirable to have tap points oriented in a same or similar direction in order to minimize the microstrip line length and routing complexity. In such an embodiment, a halfwave length delay may be added to appropriate tap points to achieve the desired response. Each lead 204A, 204B, and 204C is connected to an absorber 208A, 208B, and 208C. Each absorber 208A, 208B, and 208C is also connected to a bolometer 212A, 212B, and 212C, respectively. Readout wiring 214A, 214B, and 214C is connected to or passes through bolometers 212A, 212B, and 212C in order to transmit data read by bolometers 212A, 212B, and 212C.

Because leads 204A, 204B, and 204C are placed across different locations of slot 202, different frequencies or modes can be read out by bolometers 212A, 212B, and 212C. For example, leads 204A, 204B, and 204C can be placed across different locations of slot 202 in order for bolometers 212A, 212B, and 212C to read at desired signal frequencies (e.g., ~1.8, 5.4, and 9 THz, see FIG. 5). These frequencies correspond to extraction and detection of the $1^{st}$, $3^{rd}$ and $5^{th}$ harmonic on the slotline antenna.

For instance, with a sinusoidal excitation along the slot, for all of the modes of interest, the ends of the slots (which are electrically shorted) have zero voltage. For the first mode, half of sine-wave fits on the line, the tap is at the center. Similarly for the higher order modes, the tap points sample the waveform on the line and the signals. The tap points are located at current maximum (voltage minima). To maintain isolation between channels, this condition can be maintained for all modes. In practice, this optimization is performed numerically. It should also be noted that the absorbers in FIG. 2 can be differentially driven by the antenna (this may be required to produce a sum-beam for an even-number of current maxima on the line) or terminated with a quarter-wave stub (i.e., for a odd number of current maximum on the line). Alternatively, the orientation of the tap points could be flipped with respect to the slotline to realize the same field configuration. However, this approach may require a Radio Frequency (RF) crossover.

Figure 3:
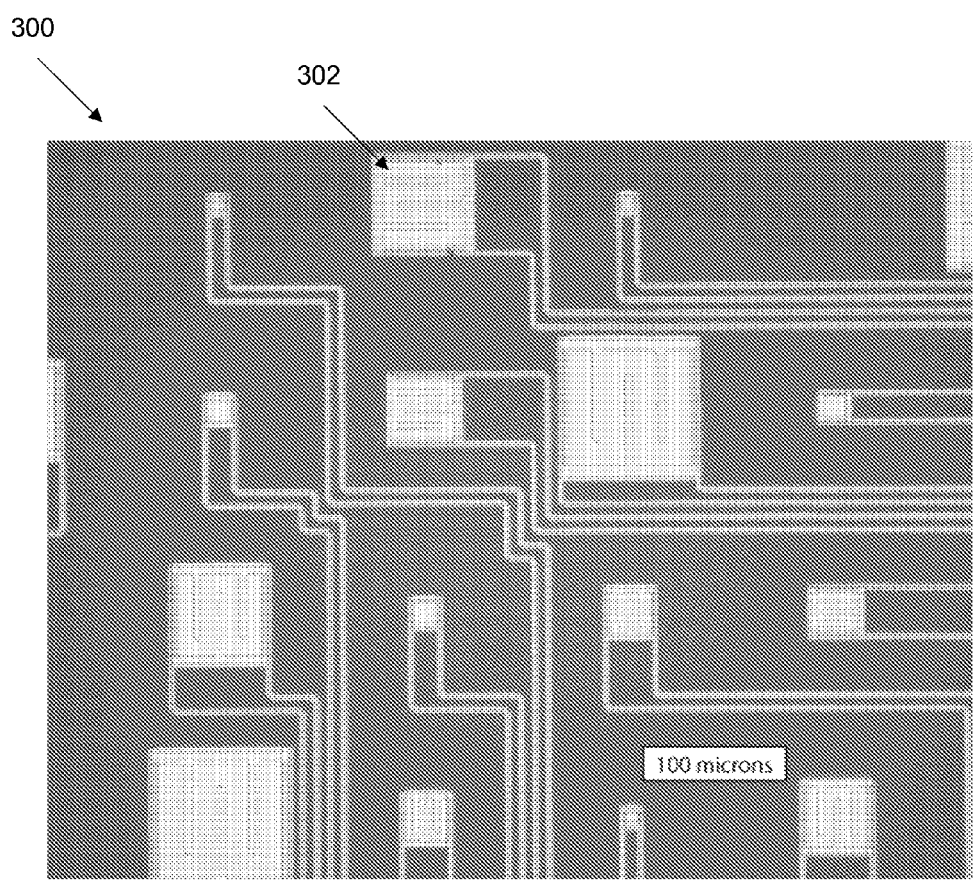
FIG. 3 illustrates a bolometer, in accordance with an embodiment of the present invention.

FIG. 3 illustrates a bolometer 300, in accordance with an embodiment of the present invention. In particular, FIG. 3 illustrates a zeptobolometer 300 (which is a type of detector technology) that reads out data from the antenna. For example, when the antenna has a current flow, the current flow heats up a small resistor (e.g., an absorber) next to the bolometer in order to allow the bolometer to read the heat from the small resistor. See FIGS. 1 and 2. Bolometer 300 can range from 12 $\mu m^2$ to greater than 100 $\mu m^2$ in some embodiments and may include a plurality of EPD or TES detectors 302. In other words, bolometer 300 can be a small bolometer, on the scale of a few microns, that is readily coupled to a metal or dielectric antenna via an impedance matching resistor (or absorber).

Figure 4:
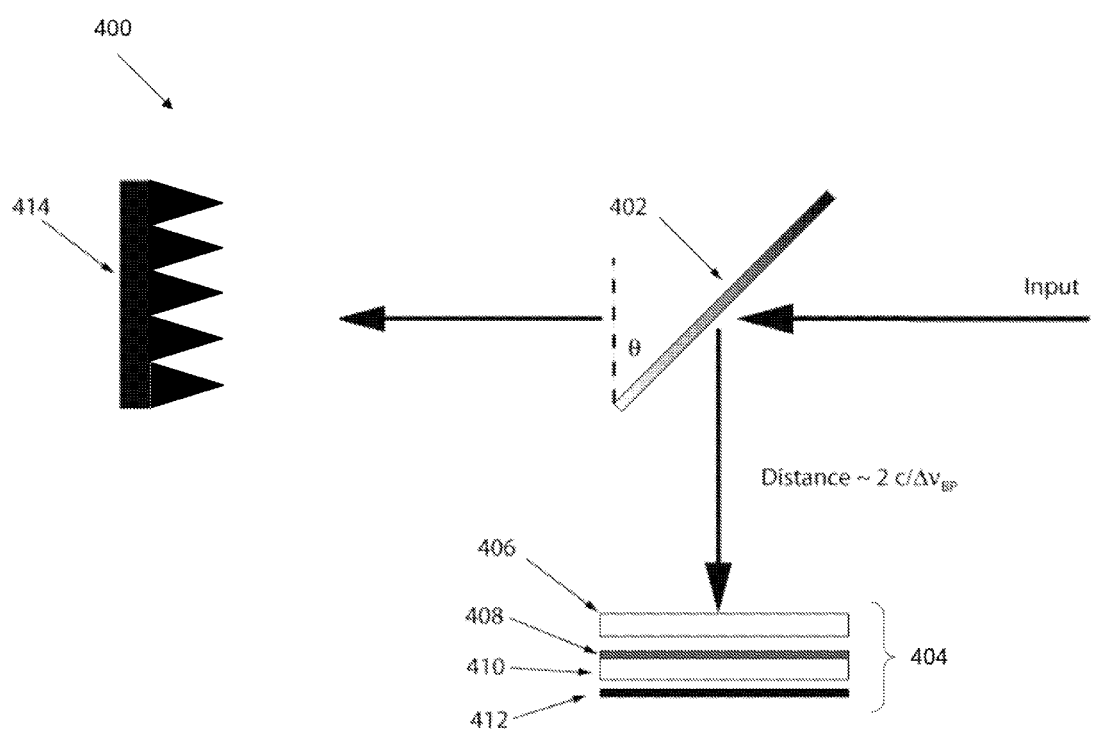
FIG. 4 illustrates a side-view of a quasioptical filter, in accordance with an embodiment of the present invention.

FIG. 4 illustrates a side-view 400 of a quasioptical filter, in accordance with an embodiment of the present invention. FIG. 4 shows a metallic grill filter 402 and a stack 404. It should be appreciated that filter 402 can be made from high purity dielectrics (e.g., float zone silicon sapphire, diamond, etc.). In this embodiment, filter 402 acts as a high pass filter to direct low pass characteristics to a location (e.g., absorber 414) where they will be absorbed. For instance, absorber 414 is configured to receive and absorb the unwanted transmitted signals in order to terminate the unwanted signals. In other words, filter 402 allows high frequency components of interest to pass through to stack 404. A person of ordinary skill in the art will readily appreciate that while there may be a single filter for all of the antennas, there may also be separate filters for each antenna in some embodiments.

In this embodiment, the angle θ of filter 402 may be greater than 45 degrees in order to minimize the difference between polarization response of filter 402. This condition minimizes the difference between the TM and TE polarization response of filter 402. It should be noted that the filter angle may be increased until the incident beam is just short of being vignetted (or partially obscured) by the focal plane array. The cutoff frequency of filter 402 is a function of the hole diameter, grill filter thickness, and hole pitch. This frequency may be the frequency at which filter 402 does not transmit radiation and may be placed above the sensor frequency bands of interest. As a result, the light incident from the telescope will reflect off filter 402 and propagate toward stack 404 to be absorbed.

It should be noted that by having the distance (e.g., 2*(speed of light in a vacuum C)/(RF signal bandwidth $\Delta v_{BP}$)) between filter 402 and the stack 404 compared to the radiation coherence length and by coating the area surrounding the sensor array with absorbing material, coherent reflections and ghosting of the image can be controlled. As a result, unabsorbed signals may reflect off the array, filter 402 and out of the telescope. Signals higher than filter cutoff frequency may propagate through filter 402 and be absorbed in a termination.

Stack 404 includes a dielectric AR coating 406, a 150-ohm resistor (or antenna) 408, a dielectric resonant absorber 410, and a metal resonant absorber (or mirror) 412. It should be appreciated that there is a vacuum gap between dielectric AR coating 406 and resistor 408 and another vacuum gap between resonant absorber 410 and resonant absorber 412. The vacuum gaps have a dielectric constant of 1 and allow light that is passed from filter 402 to resonant absorber 412 to be reflected back to filter 402. As a result, the frequencies of interest to be captured by the detectors.

It should also be appreciated that dielectric AR coating 406 is placed in front of one or more bolometers (or detectors) 410 in order to increase the absorption bandwidth. Thus, dielectric AR coating 406 is configured (or tuned) to the wavelength of the band of interest that is at the shortest wave (i.e., the highest frequency band). As a result, dielectric AR coating 406 allows absorption of radiation in the wavelength of interest.

Resonant absorbers 410 and 412 are placed behind the focal plane in order to increase quantum efficiency. For instance, resonant absorber 412, which acts as a mirror, re-reflects light that is transmitted through resistor 408 back to resistor 408 in order for the light to be absorbed by resistor 408 at the frequencies of interest.

For example, once the light passes through filter 402, the light passes through dielectric AR coating 406 and resistor (or antenna) 408. The light then reflects off of resonant absorber (or mirror) 412 and travels back to filter 402. During this process, resistor 408 absorbs the light in the targeted frequencies. It should be appreciated that dielectric coating 406, resistor 408 and resonant absorber 412 are separated by a distance in order for the bands of interest (e.g., ~1.8, 5.4, and 9 THz) to be detected by the detectors.

Figure 5:
FIG. 5 illustrates a graph that shows absorption efficiency, in accordance with an embodiment of the present invention.
Figure 5:
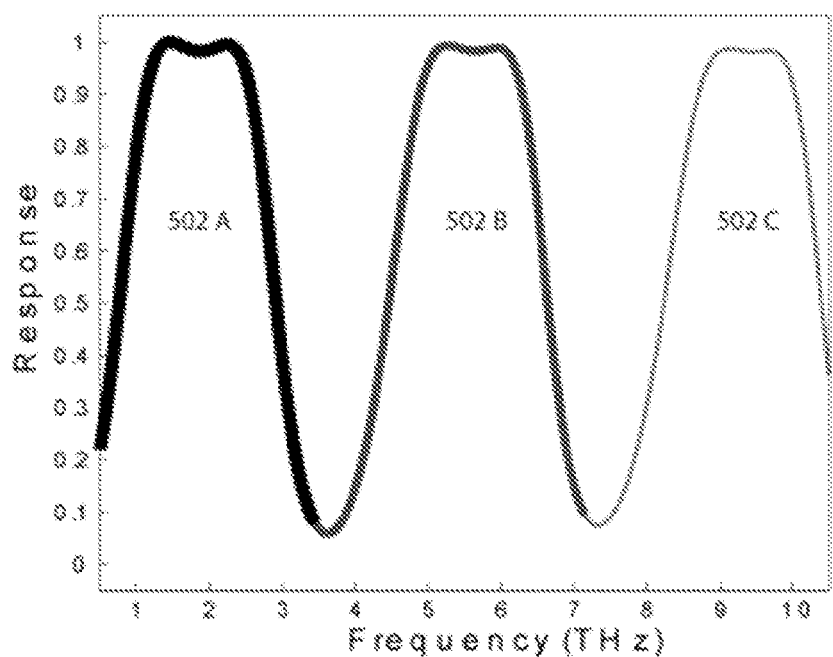

The distance between the absorber and the planar back short termination is set by the longest wavelength. For maximal absorption, the spacing can be approximately a quarter-wavelength at the center of the lowest frequency band of interest. Absorption can also occur for odd multiples of this frequency (e.g., as shown in FIG. 5, the $1^{st}$, $3^{rd}$, and $5^{th}$ harmonic) for the absorber coupled sensor array. In comparison with the antenna coupled sensor, it should be appreciated that the power in each channel is independently absorbed in separate detectors and the inter-channel isolation is limited by the details of the tap point geometry along the slotline antenna.

FIG. 5 illustrates a graph 500 that shows absorption efficiency, in accordance with an embodiment of the present invention. Graph 500 shows that the absorption in the targeted frequencies at 502A (e.g., 1.8 THz), at 502B (e.g., 5.7 THz), and 502C (e.g., 9.7 THz) are very close to one. In other words, bands at high frequencies of approximately 1.8 THz, 5.7 THz, and 9.7 THz pass through the filter.

Figure 6:
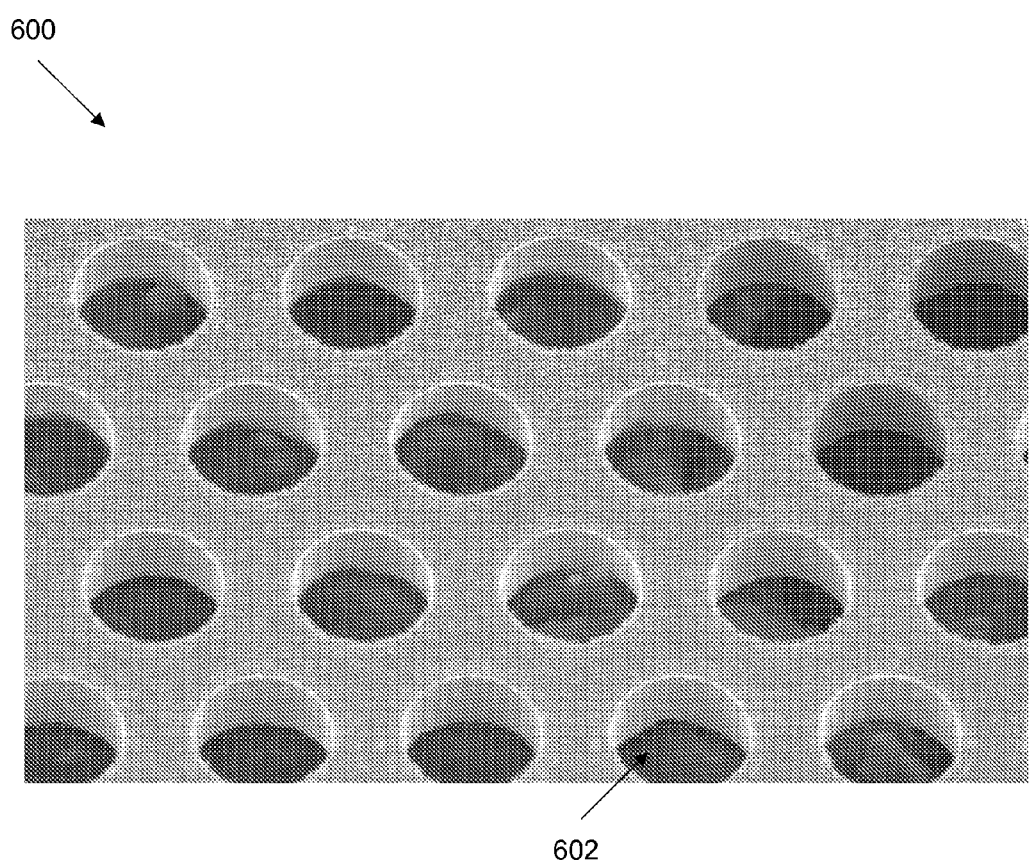
FIG. 6 illustrates a front-view of a quasioptical filter, in accordance with an embodiment of the present invention.

FIG. 6 illustrates a front-view of a quasioptical filter 600, in accordance with an embodiment of the present invention. Quasioptical filter 600 includes a plurality of holes 602. In this embodiment, plurality of holes 602 can be circular holes or square holes in order to act as a high-pass filter. This configuration allows quasioptical filter 600 to have a low-pass characteristic in reflection (and a high-pass characteristic in transmission). The frequency and reject properties of this device can be tailored by changing the hole's cross-section geometry, grill filter thickness, and hole pitch. For example, the circular holes reject any low frequency components and allow high frequency components to pass through for the antenna to absorb.

In another embodiment, plurality of holes 602 can be cross-shaped holes in order to act as a band pass filter to reject high and low frequencies. A person of ordinary skill in the art will readily appreciate that the filters can be stacked on each other with a vacuum gap between to further alter the transmittance. A person of ordinary skill in the art will also appreciate that other hole shapes may be used in other embodiments of the present invention, depending on the desired operation characteristics.

Figure 7:
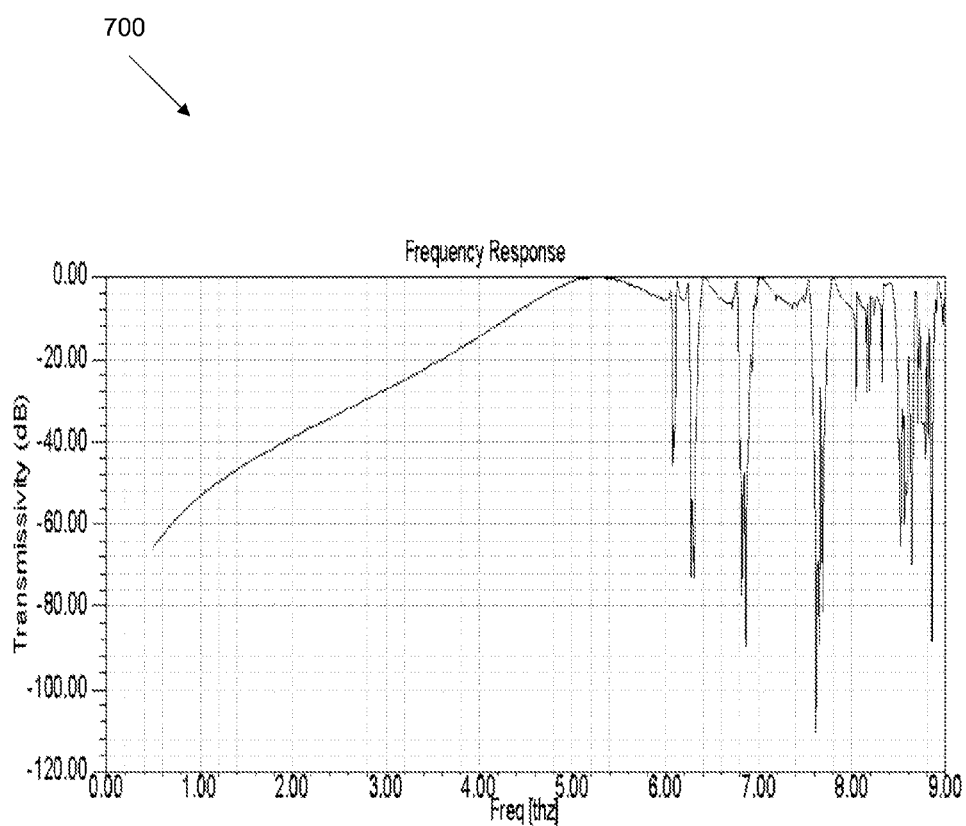
FIG. 7 illustrates a graph that shows the transmissivity versus frequency for a high pass filter, in accordance with an embodiment of the present invention.

FIG. 7 illustrates a graph 700 that shows the transmissivity versus frequency for a high pass filter, in accordance with an embodiment of the present invention. Graph 700 shows the effective frequency response over THz frequencies. For example, graph 700 shows that the frequency response peaks around 5.30 THz, which illustrates that light effectively passes (or transmits) through the filter at this frequency. Graph 700 also shows resonance around 6.10 THz, 6.30 THz, 6.80 THz, and 7.60 THz. In other words, graph 700 shows the transmissivity of a high-pass filter such that when transmissivity is near zero, then a majority (if not all) of the light passes through the filter.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus, comprising:
a filter configured to allow high frequencies of interest to pass through the filter;
an antenna configured to receive the high frequencies of interest;
a plurality of bolometers configured to measure data regarding the high frequencies of interest received by the antenna;
a dielectric coating between the antenna and the filter configured to increase an absorption bandwidth; and
a resonant absorber configured to reflect the high frequencies of interest received from the filter back to the antenna.

2. The apparatus of claim 1, wherein the filter comprises a plurality of holes configured to allow high frequencies of interest to pass through the filter.

3. The apparatus of claim 1, wherein the filter comprises a plurality of square holes configured to allow high frequencies of interest to pass through the filter.

4. The apparatus of claim 1, further comprising:
a first vacuum gap between the dielectric coating and the antenna; and
a second vacuum gap between the antenna and the resonant absorber.

5. The apparatus of claim of claim 1, wherein the antenna comprises:
one or more slots configured to receive the high frequencies of interest, and
a plurality of leads, wherein each lead operatively connects a slot to a bolometer such that the bolometer is configured to measure data regarding the high frequencies of interest.

6. The apparatus of claim 5, where the antenna is a dual slot antenna, a first slot and a second slot are separated by a distance of ~2($\lambda$/n), where $\lambda$ is a wavelength of the frequency of interest and n is an index over a fraction of the square root of the effective dielectric constant.

7. The apparatus of claim 5, where the antenna is a single slot antenna, then a length of the slot is $\lambda_{(max)}/\in_{(eff)}^{(1/2)}$, where $\lambda_{(max)}$ represents a largest wavelength intended to detect more than one frequency and $\in_{(eff)}^{(1/2)}$ represents the square root of the effective dielectric constant.

8. The apparatus of claim 1, wherein the antenna and the filter are separated by a distance based on 2*(speed of light in a vacuum)/(radio frequency signal bandwidth).

9. The apparatus of claim 1, further comprising:
wiring connecting each bolometer to an amplifier configured to transmit data read by each bolometer to the amplifier.

10. An apparatus, comprising:
a quasioptical filter configured to prevent frequencies below a cut-off from passing through the filter;
an antenna with a single slot having a plurality of tap points configured to receive and measure high frequencies of interest ranging between 1 terahertz and 10 terahertz;
a dielectric coating between the antenna and the filter configured to increase an absorption of the frequencies of interest; and
a resonant absorber configured to reflect the high frequencies of interest received from the filter back to the antenna.

11. The apparatus of claim 10, wherein the quasioptical filter comprises a plurality of circular, square, rectangular, or elliptical holes configured to allow high frequencies of interest to pass through the filter.

12. The apparatus of claim 10, further comprising:
a first vacuum gap between the dielectric coating and the antenna; and
A second vacuum gap between the antenna and the resonant absorber.

13. The apparatus of claim 10, further comprising:
a plurality of leads placed at different tap points and across the single slot in order to allow measurements at different frequencies of interest.

14. The apparatus of claim 13, further comprising:
a plurality of bolometers, each bolometer connected to a corresponding lead, and
configured to measure data regarding the frequencies of interest.

15. An apparatus, comprising:
a quasioptical filter configured to prevent frequencies below a cut-off from passing through the filter;
an antenna with a plurality of slots, each slot configured with a plurality of tap points to receive high frequencies in order to allow measurements of high frequencies of interest ranging between 1 terahertz and 10 terahertz;
a dielectric coating between the antenna and the filter configured to increase an absorption of the frequencies of interest; and
a resonant absorber configured to reflect the high frequencies of interest received from the filter back to the antenna.

16. The apparatus of claim 15, wherein the quasioptical filter comprises a plurality of circular, rectangular, square, or elliptical holes configured to allow high frequencies of interest to pass through the filter.

17. The apparatus of claim 1, wherein the antenna and the filter are separated by a distance based on 2*(speed of light in a vacuum)/(RF signal bandwidth).

* * * * *